United States Patent
Hupfer et al.

(10) Patent No.: US 11,678,850 B2
(45) Date of Patent: Jun. 20, 2023

(54) PHOTON-COUNTING X-RAY DETECTOR, MEDICAL IMAGING DEVICE AND METHOD FOR GENERATING AN X-RAY IMAGE DATA SET

(71) Applicant: Siemens Healthcare GmbH, Erlangen (DE)

(72) Inventors: Martin Hupfer, Erlangen (DE); Edgar Goederer, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/353,900

(22) Filed: Jun. 22, 2021

(65) Prior Publication Data

US 2021/0401387 A1 Dec. 30, 2021

(30) Foreign Application Priority Data

Jun. 29, 2020 (DE) .................... 10 2020 208 000.3

(51) Int. Cl.
*A61B 6/00* (2006.01)
*A61B 6/03* (2006.01)

(52) U.S. Cl.
CPC .......... *A61B 6/4241* (2013.01); *A61B 6/032* (2013.01)

(58) Field of Classification Search
CPC ............................. A61B 6/032; A61B 6/4241
See application file for complete search history.

(56) References Cited

U.S. PATENT DOCUMENTS

| 3,939,473 A | * | 2/1976 | Fuchs | ..................... H04L 27/16 |
| | | | | 375/278 |
| 4,389,989 A | * | 6/1983 | Hartig | .................. F02P 5/1551 |
| | | | | 123/339.11 |
| 4,491,942 A | * | 1/1985 | Witte | ..................... H04B 10/27 |
| | | | | 398/100 |

(Continued)

FOREIGN PATENT DOCUMENTS

DE 102008048306 B4 6/2016
DE 102009018995 B4 10/2017

OTHER PUBLICATIONS

Peizerat, A. et al.: "A 256 energy bin spectrum X-Ray photon-counting Image Sensor providing 8Mcounts/s/pixel and on-chip charge sharing, charge induction and pile-up corrections", 2017 Symposium on VLSI Circuits Digest of Technical Papers; pp. C246-C247.

(Continued)

*Primary Examiner* — Blake C Riddick
(74) *Attorney, Agent, or Firm* — Harness, Dickey & Pierce, P.L.C.

(57) ABSTRACT

A photon-counting X-ray detector includes a converter element constructed to convert incident X-rays into electrical signals in dependence on a deposition of energy in the converter element, and an evaluation device. The evaluation device includes a pulse-generator to generate and output an electrical pulse based upon an electrical signal fed from the converter element; a differentiator to generate a differentiated signal of the electrical pulse output by the pulse-generator; and a first comparator to compare the generated differentiated signal with a first threshold value and, based upon the comparison, to output a binary output signal for a period for which the threshold value is exceeded.

15 Claims, 9 Drawing Sheets

(56) References Cited

U.S. PATENT DOCUMENTS

| | | | |
|---|---|---|---|
| 4,674,023 A * | 6/1987 | Peppel | H03K 17/18 363/54 |
| 5,417,715 A * | 5/1995 | Noren | A61N 1/36521 607/9 |
| 5,586,147 A * | 12/1996 | Kreuzgruber | H03D 3/18 329/304 |
| 6,169,405 B1 * | 1/2001 | Baltzer | H01H 11/0062 324/423 |
| 6,949,962 B2 | 9/2005 | Arques | |
| 8,422,627 B2 | 4/2013 | Kappler | |
| 9,081,103 B2 | 7/2015 | Loeliger | |
| 10,126,167 B2 | 11/2018 | De Geronimo | |
| 2005/0224055 A1 * | 10/2005 | Wiese | F02D 41/0025 73/114.39 |
| 2010/0270473 A1 | 10/2010 | Kraft et al. | |
| 2016/0077148 A1 | 3/2016 | Kimura et al. | |
| 2017/0035376 A1 | 2/2017 | Surendranath et al. | |
| 2017/0086761 A1 | 3/2017 | Fu et al. | |
| 2018/0252821 A1 | 9/2018 | Svensson et al. | |
| 2019/0033469 A1 | 1/2019 | Brambilla et al. | |
| 2019/0120975 A1 | 4/2019 | Ouvrier-Buffet | |

OTHER PUBLICATIONS

Rostaing, J.P. et al.: "ADC sampling reduction by an efficient implementation of queue application to X-ray spectrometry imagers", Electronics Letters, vol. 52, No. 6, pp. 428-430, 2016; publicly available at: https://ietresearch.onlinelibrary.wiley.com/doi/epdf/10.1049/el.2015.4306.

* cited by examiner

PHOTON-COUNTING X-RAY DETECTOR, MEDICAL IMAGING DEVICE AND METHOD FOR GENERATING AN X-RAY IMAGE DATA SET

PRIORITY STATEMENT

The present application hereby claims priority under 35 U.S.C. § 119 to German patent application number DE 102020208000.3 filed Jun. 29, 2020, the entire contents of which are hereby incorporated herein by reference.

FIELD

Example embodiments of the invention generally relate to a photon-counting X-ray detector, a medical imaging device having a photon-counting X-ray detector, and a method for generating an X-ray image data set via a photon-counting X-ray detector.

BACKGROUND

Photon-counting X-ray detectors are used in many imaging applications. For example, these X-ray detectors may be utilized in medical imaging, for example in computed tomography scanners, to generate a tomographic X-ray image of a region undergoing examination in a patient.

A photon-counting X-ray detector that can be used is in particular a photon-counting, direct-conversion X-ray detector. In such X-ray detectors, incident X-rays or photons may be converted into electrical pulses by a suitable converter material. Examples of converter material that may be used are CdTe, CZT, $HgI_2$, GaAs or other materials. The electrical pulses are evaluated by an evaluation electronics unit, for example an integrated circuit (application specific integrated circuit, ASIC). In X-ray detectors that count, incident X-rays are measured by counting the electrical pulses that are triggered by the absorption of X-ray photons in the converter material, and said X-rays are used as an image signal. The height or indeed the length of a generated electrical pulse is typically proportional to the energy of the absorbed X-ray photon. This allows an item of spectral information to be extracted by comparing the height or length of the electrical pulse with the energy threshold. Frequently, photon-counting X-ray detectors have a plurality of adjustable energy thresholds for comparing the electrical pulses generated, with the result that energy-resolved measurements depending on a plurality of energy ranges defined by the energy thresholds are made possible.

In particular in the case of the high levels of photon flux that may occur in X-ray imaging and in particular in computed tomography, there may be an overlaying of the electrical pulses generated, the so-called pile-up of generated pulses, as a result of which false pulse heights or lengths result, or indeed the detector is even paralyzed, with the generated pulses no longer falling below the level of the predetermined energy thresholds. Consequently, pile-up results in a false number of counted photon events, and with energy-resolved measurements also in a false measurement of energy, and in the case of very high levels of photon flux this may even result in a measurement signal that is unusable for generating X-ray images.

A series of measures exists that counter the effects of pile-up. One simple possibility consists in a reduction in the pixel size and the concomitant reduction in the photon flux that is to be processed by an individual pixel element. However, this has a disadvantageous effect for example as a result of increased charge sharing—that is to say dividing up an event over a plurality of mutually adjacent pixel elements. Other possibilities consist for example in implementing switches that detect the occurrence of pile-up, or at least enable an assessment of the effects this has on the measurement signals.

For example, DE 10 2008 048 306 B4 discloses a method for detecting X-rays from an X-ray emitter, wherein at least one threshold energy for comparing a signal, generated in dependence on the photon energy, in the X-ray detector is predetermined, this threshold energy being greater than the maximum energy of the X-ray spectrum emitted by the X-ray emitter, with the result that events affected by pile-up can be detected.

DE 10 2009 018 995 B4 discloses a detector having a multiplicity of direct-conversion detector elements, wherein generated signal pulses are fed on the one hand to a pulse height analyzer that operates continuously at a predetermined energy threshold and on the other to a pulse height analyzer that operates at a predetermined energy threshold and at a predetermined clock frequency, and are then detected in a combined logistical unit, wherein the clocked pulse height analyzer is intended to prevent excessive underestimation of the count rate.

US 2019/001 209 75 discloses a circuit for counting photons, including a digital stage that comprises at least one comparator for comparing generated pulse amplitudes with a threshold value, a differentiator circuit for determining periods in which the derivative of the pulse signal is of a given sign, and a logic gate for combining the outputs of the comparator and the differentiator circuit, wherein the pulses present are counted at the output of the combining element.

SUMMARY

In this context, at least one embodiment of the invention takes as its starting point the observation that higher-quality imaging and more flexible use of an X-ray detector would be possible if the effect of pile-up on the information detected by the X-ray detector could be reduced even at high X-ray photon rates.

At least one embodiment of the invention provides an improved photon-counting X-ray detector in order to enable higher-quality imaging and more flexible use of the photon-counting X-ray detector.

Further advantageous embodiments and developments of the invention, some themselves inventive, appear in the claims and the description below.

At least one embodiment of the invention relates to a photon-counting X-ray detector, having a converter element constructed to convert incident X-rays into electrical signals in dependence on a deposition of energy in the converter element, and an evaluation unit coupled thereto, having a pulse-generating unit that is constructed to generate and output an electrical pulse based upon an electrical signal fed from the converter element, a differentiator unit, coupled to the pulse-generating unit and constructed to generate a differentiated signal of the electrical pulse that is output by the pulse-generating unit, and a first comparator, coupled to the differentiator unit and constructed to compare the generated differentiated signal with a first threshold value and, based upon the comparison, to output a binary output signal for a period for which the threshold value is exceeded.

Moreover, at least one embodiment of the invention relates to a medical imaging device, comprising a photon-counting X-ray detector according to one of the above-described variant embodiments and comprising, in a position opposite it, an X-ray source for exposing the X-ray detector to X-rays.

Moreover, at least one embodiment of the invention relates to a method for generating an X-ray image data set via a photon-counting X-ray detector, which has a converter element that is constructed to convert incident X-rays into electrical signals in dependence on a deposition of energy in the converter element, and an evaluation unit coupled thereto, for processing the electrical signals, wherein the X-ray image data set is generated based upon the processed electrical signals, and during processing electrical pulses are generated via a pulse-generating unit based upon electrical signals fed from the converter element, a differentiated signal of a respective pulse that is generated by the pulse-generating unit is generated via a differentiator unit that is coupled thereto, the differentiated signal is compared with a first threshold value, via a first comparator that is coupled to the differentiator unit, and a binary output signal is output based upon the comparison for a period for which the threshold value is exceeded, wherein the binary output signal of the first comparator is input to the generation of the X-ray image data set.

Moreover, at least one embodiment of the invention relates to a photon-counting X-ray detector, comprising:
a converter element to convert incident X-rays into electrical signals in dependence on a deposition of energy in the converter element; and
an evaluation device coupled to the converter, the evaluation device including:
  a pulse-generator, to generate and output an electrical pulse based upon an electrical signal fed from the converter element,
  a differentiator, coupled to the pulse-generator, to generate a differentiated signal of the electrical pulse output by the pulse-generator, and
  a first comparator, coupled to the differentiator, to compare the differentiated signal generated with a first threshold value and, based upon the comparison, to output a binary output signal for a period for which the first threshold value is exceeded by the differentiated signal generated.

Moreover, at least one embodiment of the invention relates to a medical imaging device, in particular a computed tomography device, comprising:
the photon-counting X-ray detector of an embodiment; and
an X-ray source, in a position opposite to the photon-counting X-ray detector, for exposing the X-ray detector to X-rays.

Moreover, at least one embodiment of the invention relates to a method, using a photon-counting X-ray detector including a converter element to convert incident X-rays into electrical signals in dependence on a deposition of energy in the converter element and an evaluation unit for processing the electrical signals, the method comprising:
generating electrical pulses via a pulse-generator based upon electrical signals fed from the converter element;
generating a respective differentiated signal of a respective pulse, of the electrical pulses generated by the pulse-generating unit, via a differentiator;
comparing each respective differentiated signal with a first threshold value, via a first comparator; and
outputting a binary output signal based upon the comparing of the respective differentiated signals, for a period for which the first threshold value is exceeded by a respective differentiated signal, wherein the binary output signal of the first comparator is usable for generation of an X-ray image data set.

BRIEF DESCRIPTION OF THE DRAWINGS

The invention is explained below with reference to example embodiments, with reference to the attached figures. The illustration in the figures is schematic, highly simplified and not necessarily to scale. In the drawings.

DETAILED DESCRIPTION OF THE EXAMPLE EMBODIMENTS

Figure 1:
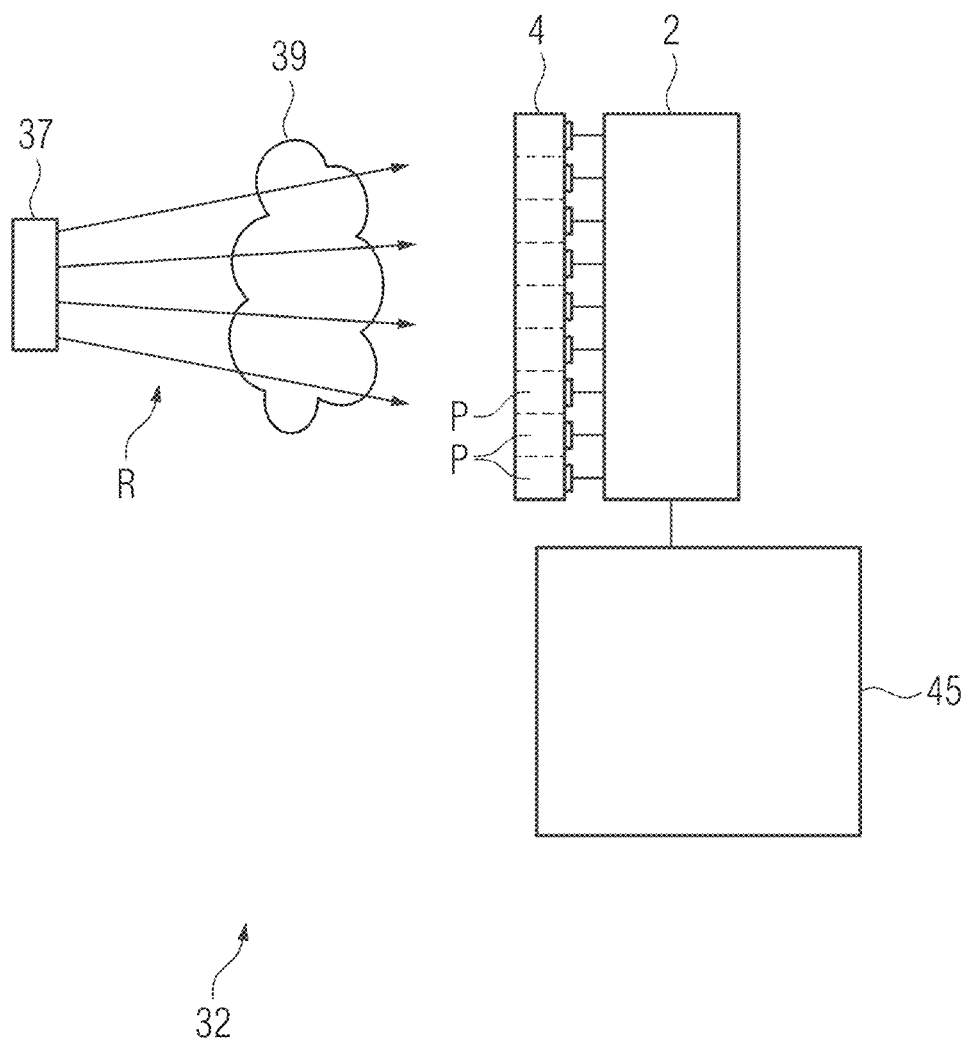
FIG. 1 shows a schematic representation of a medical imaging device with a photon-counting X-ray detector, FIGS. 2 to 4 provide an illustration in the form of graphs of resulting signal sequences, in response to X-rays that meet a photon-counting X-ray detector.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a photon-counting X-ray detector, having a converter element constructed to convert incident X-rays into electrical signals in dependence on a deposition of energy in the converter element, and an evaluation unit coupled thereto, having a pulse-generating unit that is constructed to generate and output an electrical pulse based upon an electrical signal fed from the converter element, a differentiator unit, coupled to the pulse-generating unit and constructed to generate a differentiated signal of the electrical pulse that is output by the pulse-generating unit, and a first comparator, coupled to the differentiator unit and constructed to compare the generated differentiated signal with a first threshold value and, based upon the comparison, to output a binary output signal for a period for which the threshold value is exceeded.

The photon-counting X-ray detector that is used in the context of at least one embodiment of the invention may also be designated a counting direct-conversion X-ray detector. Direct-conversion X-ray detectors are usually made in a stacked construction in which there is attached to the underside of a layer of a converter material—that is to say of the converter element—an associated evaluation unit, for example in the form of an ASIC (application specific integrated circuit).

Optionally, there may moreover be arranged between the evaluation unit and the converter element an intermediate element—an interposer—that can serve to stabilize or indeed to divert signal lines. The underside of the converter element conventionally has a plurality of electrodes in the form of metallized contact elements. These allow the evaluation unit to be brought into contact for signal transmission, conventionally being soldered.

Conventionally in this case, opposite each contact element on the converter side there is a counter-contact element, in pixel form, on the evaluation unit side. In a conventional configuration, the evaluation unit provides pixel electronic equipment for pixel-by-pixel processing of a signal input via the electrodes.

In the converter material of the converter element, in dependence on the energy of an X-ray photon deposited locally, incident X-rays are converted into charge carriers, based upon which a signal is generated and further processed in the pixel-by-pixel pixel electronic equipment. A pixel element of a photon-counting X-ray detector can then be interpreted as comprising respective pixel-by-pixel pixel electronic equipment of the evaluation unit and a detector volume in the converter element that is associated with the pixel element and is formed by the electrical field between a respective electrode on the converter side and a top electrode mounted on the opposite side of the converter element.

Typically, a pulse-generating unit is associated with each such pixel element of a photon-counting X-ray detector. This means that, typically, the evaluation unit has a plurality of pulse-generating units. A pulse-generating unit may have in particular a signal amplifier and a pulse shaper. The pulse-generating unit serves to amplify the signal that is input to pixel electronic equipment by way of an electrode and to output an analog signal pulse whereof the pulse amplitude and/or pulse length depends on the charge carriers generated by deposition of the energy of an incident X-ray photon in the detector volume of the converter element that is associated with the pulse-generating unit in question.

According to at least one embodiment of the invention, the analog signal output by the pulse-generating unit is now output to the differentiator unit and differentiated such that the signal that is output by the differentiator unit represents a derivative of the signal output by the pulse-generating unit. Using the derivative—that is to say, of the differentiated signal—information on the signal characteristic—that is to say, for example, on rising or falling sections—of the signal that is output by the pulse-generating unit can be provided. If for example pulses generated by the pulse-generating unit are overlaid before the primary pulse—the one generated by the pulse-generating unit—has decayed, then any new rise in the signal that may occur can be detected via the differentiated signal. Based on the differentiated signal, information that is relatively independent of pile-up, or an indication of pile-up occurring, can consequently advantageously be derived and utilized to generate an X-ray image data set. For example, analysis of the differentiated signal can supply a better indication of an actual number of incident photons. The differentiator unit may take different forms. By way of example, it comprises a circuit that determines the sign (positive or negative) of the rise in the signal that the pulse-generating unit outputs by analog means.

According to at least one embodiment of the invention, the differentiated signal is furthermore output to a first comparator, which has a signal link to the differentiator unit and is used to compare the differentiated signal with the first threshold value and, based upon the comparison, to output a binary signal. The differentiated signal is consequently digitized via the first threshold value for simple and, where appropriate, also direct further processing. Preferably, the first threshold value is applied taking into consideration the electronic noise of the X-ray detector. As a result, advantageously it is possible to make the derived signal that is output by the differentiator unit robust in the face of the presence of electronic noise. Preferably, the first threshold value is set just above the electronic noise value of the X-ray detector, with the result that the greatest possible sensitivity is achieved in the generation of the binary signal while simultaneously suppressing noise. Each binary signal that is output may in particular have a duration corresponding to the respective period for which the first threshold value is exceeded by the differentiated signal.

It is possible, in a photon-counting X-ray detector having a plurality of pixel elements, for there to be associated in particular with each pixel element of the X-ray detector a pulse-generating unit, a differentiator unit and a first comparator. As an alternative, it may also be provided for only one pixel element of a group of pixel elements, for example only every second or third pixel element of the X-ray detector, to be formed with a differentiator unit and for determined information based on a differentiated signal, for example for the correction of a number of incident photons that are counted or the adaptation of adjustment parameters, to be transferred to the pixel elements of a group.

It is advantageously possible for the binary signal that is based on the differentiated signal to be input to an X-ray image data set generated via the photon-counting X-ray detector according to the invention, in order to obtain a higher-quality X-ray image data set or indeed, in situations of extreme flux levels, to obtain more reliable image information. In particular, this may be used for example to determine a better estimation of a counted number of incident X-ray photons in a respective pixel element of the photon-counting X-ray detector, or to enable better counting of the number itself.

Moreover, the pulse-generating unit may have a signal link to at least one second comparator, constructed to compare an electrical pulse that is generated by the pulse-generating unit with a second threshold value. In particular, each pixel element of an X-ray detector may comprise at least one second comparator. Linking a comparator to the pulse-generating unit in this way is substantially generally known in the context of conventional signal processing in a photon-counting X-ray detector. For the purpose of counting a number of incident photons, it is then possible, based upon a comparison from the second comparator, to output a second binary signal as the count signal. This means that as soon as an analog electrical signal pulse that is generated by the pulse-generating unit exceeds the second threshold value, a count signal can be output via the second comparator. The count signal can then be counted via a counting unit (counter) that has a signal link to the second comparator and takes the form for example of a rising-edge counter or falling-edge counter. Moreover, the length of the second binary signal that is output can correspond to the duration for which the generated analog electrical pulse exceeds the second threshold value.

Likewise, a plurality of second comparators, each having an associated threshold value and each coupled to the pulse-generating unit, may be provided. If the plurality of threshold values of the second comparators is suitably adjusted and the generated pulses are counted depending on the threshold values, then it is possible to obtain energy information on the incident X-ray photons in a plurality of energy channels that are defined by the energy thresholds.

In a preferred variant embodiment of the photon-counting X-ray detector, the evaluation unit has at least one such second comparator, which is coupled to the pulse-generating unit and is constructed to compare an electrical pulse generated by the pulse-generating unit with a second threshold value. The duration for which the generated electrical pulse exceeds the second threshold value substantially corresponds to the period of time over which a subsequent occurring event is not detected as a separate event.

Moreover, in this variant the photon-counting X-ray detector has a determination unit, which is constructed to determine, at least while an electrical pulse generated by the pulse-generating unit lies above the second threshold value of the second comparator, a sequence of the first binary output signal that is based on the differentiated signal.

The determined sequence of the first binary signal based on the differentiated signal can be utilized to detect the overlaying of pulses and consequently to determine an improvement in the number of incident photons, or to correct a number of incident photons that have been counted based upon a second binary signal. The sequence may comprise the time characteristic of the first binary signal over time. The sequence may for example also comprise the number of falling and/or rising edges of the first binary signal.

By analyzing the sequence of the first binary signal, with regular counting based on the signal pulse that is directly output by the pulse-generating unit and the associated second binary signal, it is possible to infer non-counted events. By creating a link with the fact that the signal pulse exceeds the second threshold, the data capture during a measurement sequence and the subsequent analysis can advantageously be restricted to the signals that are relevant to image generation in dependence on the second threshold.

Moreover, outputting and storing the determined sequence in each case while an electrical pulse generated by the pulse-generating unit lies above the second threshold may advantageously enable subsequent correction within the context of post-processing detected count rates, based on the electrical pulses that are generated by the pulse-generating unit. In this case, however, there should preferably be a time link between the determined sequence and the detected data, at least based on a read-off period, in order to enable optimal subsequent correction of detected count rates.

Furthermore, the photon-counting X-ray detector according to at least one embodiment of the invention may have a first counter that is coupled to the first comparator and is constructed to count a number of rising or falling edges of binary output signals that are output by the first comparator.

Implementation of this kind may advantageously be utilized for example to already obtain a better measure of the photon flux during or directly after an ongoing measurement, without subsequent evaluation of a sequence of the binary signal.

In variant embodiments, a measure of photon flux may also be determined without a link to the fact that a second threshold value has been exceeded in a second comparator, and the complexity of the circuit may thus be reduced. Information of this kind may advantageously be utilized to select adjustment parameters for data capture with the X-ray detector while a measurement sequence is still going on, or indeed to select image generation parameters in the generation of an X-ray image data set based on the measurement data, in a suitable way. Because a determination based on the differentiated signal is less affected by pile-up, it is possible, based on the counted number of rising or falling edges of the first binary output signal, to draw better conclusions on better adjustments even when there are very high levels of photon flux.

In a development of this, the photon-counting X-ray detector has an adapter unit, constructed to adapt the generation of electrical pulses in the pulse-generating unit based upon the number of rising or falling edges that have been counted using the first counter.

The adapter unit may be provided such that it is individually controllable for each pixel element—that is to say for each pulse-generating unit—and may enable the pixel-specific control and adaptation of a respective pulse-generating unit of a respective pixel element, in order to ensure an adaptation that is as spatially resolved as possible, based on the prevailing conditions. It is then possible to base the adaptation directly on the number of rising or falling edges of the first binary signal that have been counted in a respective pixel element, provided this number is determined individually in each pixel element. The adapter unit may also be provided an inter-pixel adaptation of the pulse-generating units of a plurality of pixel elements, wherein, based on the counted numbers of rising or falling edges of the first binary signal in at least one pixel element of the plurality of pixel elements, there is a common adaptation of the pulse-generating units for the plurality of pixel elements. This can enable simplified implementation of the circuits.

For example, the transfer function of the pulse-generating unit during a measurement sequence can be adapted to a current photon flux or to a photon flux that is expected in the future. For example, a decay time, a rising time or an amplification of an electrical signal pulse that is generated via the pulse-generating unit can be adapted. Shortening a generated electrical pulse may for example result in reduced occurrence of the overlaying of pulses and hence in reduced pile-up. At the same time, however, this may negatively amplify the electronic noise of the X-ray detector, for example, or have a negative effect on energy resolution. Adapting the pulse generation in the pulse-generating unit in dependence on a photon flux makes it possible to select an optimal adjustment for the pulse generation, both with low levels of photon flux and also with high levels of photon flux, and hence always to obtain the highest-quality image information possible in the respective conditions. Here, it appears advantageous that the first binary signal based on the differentiated signal is less affected by pile-up than the output signal of the pulse-generating unit or the second comparator itself that is coupled thereto, and hence displays better linearity behavior compared with this output signal, right up to very high levels of photon flux. In this way, advantageously better adjustability can be made possible.

Here, however, it has to be taken into account that when the pulse-generating unit is adapted, other settings of the X-ray detector and its circuits typically also have to be adapted. For example, if the pulse-generating unit is adapted, it may be the case that the first and/or second threshold value of the first and/or second comparator also has to be adapted at the same time. Similarly, it may be that a change in the electronic noise also has to be taken into account.

Advantageously, however, as a result it can be ensured that the linearity behavior of the X-ray detector is better, even at high levels of flux. Advantageously, this can result directly and instantly, during an ongoing measurement, in an improvement in the captured data and hence in a higher-quality X-ray image data set.

Furthermore in this case, the pulse-generating unit may have a first pulse generation channel, a second pulse generation channel, and a switch element that is constructed to switch at least between the first pulse generation channel and the second pulse generation channel, for the purpose of generating the electrical pulses. In that case, the adapter unit can be constructed to switch over the switch element based upon the number of rising or falling edges that have been counted via the first counter.

The second pulse generation channel may have a shorter pulse shaping time than the first pulse generation channel, which results in shorter signal pulses with the same deposited energy and hence in the capacity to distinguish better between photon events that succeed one another rapidly. Longer pulse shaping times, by contrast, typically result in less electronic noise and hence in better energy resolution of a photon energy that is to be determined.

The first pulse generation channel and the second pulse generation channel may be adjusted differently from one another using adjustment parameters, for example before the X-ray detector is used, or indeed may be permanently and differently set in the evaluation unit. While the photon-counting X-ray detector is in use, switchover is in that case only between the pre-adjusted or permanently set pulse generation channels. For example, a threshold value may be defined based upon the number of rising or falling edges that have been counted by the first counter, wherein there is a switchover from the first to the second pulse generation channel or vice versa if the threshold value is exceeded or fallen below. Here, it is also possible to provide more than two pulse generation channels.

This variant may advantageously correspond to applying an adjustment to the pulse generation channel, based on the number that are counted, in a simple manner that can be well controlled. The restriction to a limited number of pulse generation channels, and adaptation in the form of switching between the pulse generation channels, here is advantageously accompanied by a limitation, in respect of the complexity of lifting and the scope of use of the X-ray detector, on the adjustment and calibration data to be provided.

In a further variant embodiment of the photon-counting X-ray detector, the evaluation unit is moreover constructed to determine in each case the duration of a binary output signal that is output by the first comparator.

The duration of a binary output signal that is output may be presented for example in the form of a so-called time-over-threshold measurement, as is widely known in the specialist field of photon-counting X-ray detectors. Here, the duration for which the threshold value of a comparator is exceeded is determined from a comparison between the binary signal that is output and an external clock signal, and expressed in units of the beats of the clock signal.

The inventors have seen that determination of a duration of a binary output signal that is output by the first comparator—that is to say based on the differentiated signal—can also advantageously be utilized for input to the image data generation. The determined durations have a correlation with the energy of the incident photons and can, in particular in the event of high levels of flux, deliver information that is less affected by pile-up than the evaluation of the primary signal of the pulse generation unit.

In a further development of this, the X-ray detector is moreover constructed to define an integral over the durations or an average of the durations of a plurality of successive binary output signals within a time interval.

The inventors have seen that this value can have a high degree of correlation with the energy flux of the X-ray field and, in particular in the event of a high level of flux, can provide information that is similar to a conventional energy-integrating detector and can be used accordingly to generate an X-ray image data set. Here, the time interval preferably corresponds substantially to a respective read-off time window of the X-ray detector. In that case it is conceivable that this information can, in particular in the case of high flux, be input at least to the image generation in order still to obtain relatively reliable image information even in extreme capture conditions.

Moreover, at least one embodiment of the invention relates to a medical imaging device, comprising a photon-counting X-ray detector according to one of the above-described variant embodiments and comprising, in a position opposite it, an X-ray source for exposing the X-ray detector to X-rays.

Here, the features and advantages of the photon-counting X-ray detector are directly applicable to the medical imaging device.

In that case, for capture of the X-ray image data set, the object to be imaged can in particular be placed between the X-ray source and the X-ray detector and irradiated by the X-ray source.

Conventionally, the medical imaging device comprises at least one photon-counting X-ray detector according to the invention and, in a position opposite it, at least one X-ray source, for example an X-ray tube. However, the imaging device may also comprise a plurality of X-ray detectors according to the invention.

In particular, the medical imaging device may also take the form of a computed tomography system. However, it may also take the form for example of a C-frame X-ray device and/or Dyna-CT or take another form.

Moreover, at least one embodiment of the invention relates to a method for generating an X-ray image data set via a photon-counting X-ray detector, which has a converter element that is constructed to convert incident X-rays into electrical signals in dependence on a deposition of energy in the converter element, and an evaluation unit coupled thereto, for processing the electrical signals, wherein the X-ray image data set is generated based upon the processed electrical signals, and during processing electrical pulses are generated via a pulse-generating unit based upon electrical signals fed from the converter element, a differentiated signal of a respective pulse that is generated by the pulse-generating unit is generated via a differentiator unit that is coupled thereto, the differentiated signal is compared with a first threshold value, via a first comparator that is coupled to the differentiator unit, and a binary output signal is output based upon the comparison for a period for which the threshold value is exceeded, wherein the binary output signal of the first comparator is input to the generation of the X-ray image data set.

The input may comprise a correction or adaptation, via at least a second comparator, of counted numbers of signal pulses that are generated by the pulse-generating unit, wherein the image values that the generated X-ray image data set comprises are then based on the adapted numbers. The input can also comprise, based on the first binary signal, adapting adjustment parameters of the X-ray detector, wherein the adjustment results in better collection of the measurement data utilized for image generation. The input can also comprise basing the image generation only on the first binary signal or information derived therefrom. That is to say that in this case the image values that the generated X-ray image data set comprises may also be based exclusively on the first binary signal.

The above-described advantages of the X-ray detector according to at least one embodiment of the invention are in this case also readily applicable to the method for generating an X-ray image data set via a photon-counting X-ray detector and, accordingly, to the variants described below.

According to a development of the method for generating an X-ray image data set, and wherein the evaluation unit is constructed to determine in each case the duration of a binary output signal that is output by the first comparator, an integral or an average of the durations of a plurality of successive binary output signals of the first comparator is defined via a defining unit, and the X-ray image data set is generated based upon the integral or average.

In a further variant embodiment of the method for generating an X-ray image data set, a number of rising or falling edges of binary output signals that are output by the first comparator are counted via a counter that is coupled to the first comparator, and the generation of electrical pulses in the pulse-generating unit is adapted via an adapter unit, based upon the number of rising or falling edges that have been counted.

Furthermore, a method variant on the method for generating an X-ray image data set may comprise using a second comparator, which is coupled to the pulse-generating unit, to compare an electrical pulse that is generated by the pulse-generating unit with a second threshold value and, on this basis, outputting a second binary output signal, using a second counter, which is coupled to the second comparator, to count a number of rising or falling edges of second binary output signals that are output, using a determination unit to determine a sequence of the first binary output signal at least while an electrical pulse that is generated by the pulse-generating unit lies above the second threshold value of the second comparator, and adapting the counted number of generated electrical pulses for the purpose of generating the X-ray image data set based upon the determined sequence.

In the context of the invention, in particular features that are described in relation to different embodiments of the invention and/or different claims categories (method, use, device, system, arrangement, etc.) can be combined to form further embodiments of the invention. For example, a claim that relates to a device may also be developed using features that are described or claimed in conjunction with a method, and vice versa. Functional features of a method may in this context be performed by correspondingly constructed concrete components. As well as the embodiments of the invention that are explicitly described in this application, also conceivable are numerous further embodiments of the invention that those skilled in the art may arrive at without departing from the scope of the invention that is specified by the claims.

The use of the indefinite articles "a" and "an" does not rule out the possibility that the feature concerned may also be present a plurality of times. The use of the expression "have" does not rule out the possibility that the terms linked by the expression "have" may be identical. For example, the medical imaging apparatus has the medical imaging apparatus. The use of the expression "unit" does not rule out the possibility that the item to which the expression "unit" relates may have a plurality of components that are spatially separated from one another.

The expression "based on" or "based upon" may, in the context of the present application, be understood in particular in the sense of the expression "using". In particular, wording according to which a first feature is generated (or alternatively determined, defined, etc.) based upon a second feature does not rule out the possibility that the first feature may be generated (or alternatively determined, defined, etc.) based upon a third feature.

For the sake of clarity, in the text below only the elements that are useful for an understanding of the described embodiments are shown. In particular, the formation of a photon-counting X-ray detector that uses one or more circuits for counting incident photons is not shown in detail, since the described embodiments are compatible with the current construction of such systems. Nor are the construction and formation of circuits provided upstream of the counting circuit, or the formation of X-ray detectors made of semiconductor material, described in detail, the described embodiments being substantially compatible with conventional implementations of such detectors and circuits.

FIG. 1 is a highly simplified representation of an imaging device 32 based on ionizing radiation R.

A medical imaging device 32 of this kind generally consists of a radiation source 37, frequently an X-ray tube, for emitting ionizing radiation R, in particular X-rays. A photon-counting X-ray detector having a converter element 4 and an evaluation unit 2 is arranged opposite the radiation source 37. An object undergoing examination 39 is arranged between the radiation source 37 and the X-ray detector such that the radiation R emitted by the radiation source 37 penetrates the object 39 and is attenuated thereby, in dependence on the nature of the object 39, before reaching the X-ray detector.

The photon-counting X-ray detector may in particular have a plurality of pixel elements P for spatially resolved measurement of the incident X-rays. Associated with a pixel element P there may be a detector volume in the converter element 4, and pixel electronic equipment (which may typically be associated pixel by pixel) for the purpose of pixel-by-pixel processing of the signals fed from the converter element 4 to the evaluation unit 2.

The signals processed by the evaluation unit 2 are processed further, usually by a processor unit 45, to give an X-ray image data set. The processor unit 45 may contain user interface apparatuses (such as one or more display units in the form of screens, one or more input/output apparatuses in the form of a keyboard, mouse or another type), storage elements or similar.

The converter element 4 includes a converter material that is suitable for converting incident X-rays into electrical signals in dependence on the energy deposited in the converter element 4. The converter element 4 includes in particular a direct-conversion semiconductor material, such as CdTe, CZT, HgI$_2$, GaAs or other materials.

Conventionally, there is associated with each pixel element P a pulse-generating unit 6, which is constructed to generate and output an electrical pulse S in response to the energy deposited by an X-ray photon in the converter element 4 and thus based upon an electrical signal fed from the converter element 4.

According to an embodiment of the invention, the evaluation unit 2 also has a differentiator unit 10 that is coupled to the pulse-generating unit 6 and is constructed to generate a differentiated signal dS of the electrical pulse S that is output by the pulse-generating unit 6. Furthermore, the differentiator unit 10 has a signal link to a first comparator 8 that is constructed to compare the generated differentiated signal dS with a first threshold value TH1 and, based upon the comparison, to output a binary output signal K1 for a period for which the threshold value TH1 is exceeded.

Figure 2:
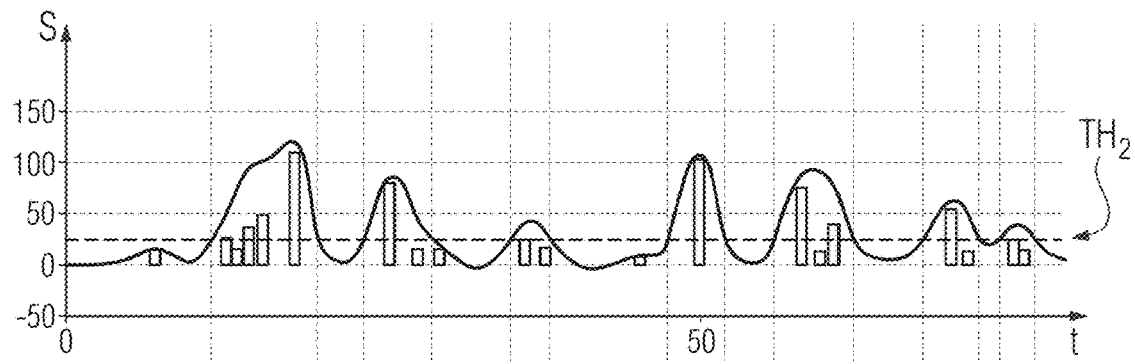
Figure 3:
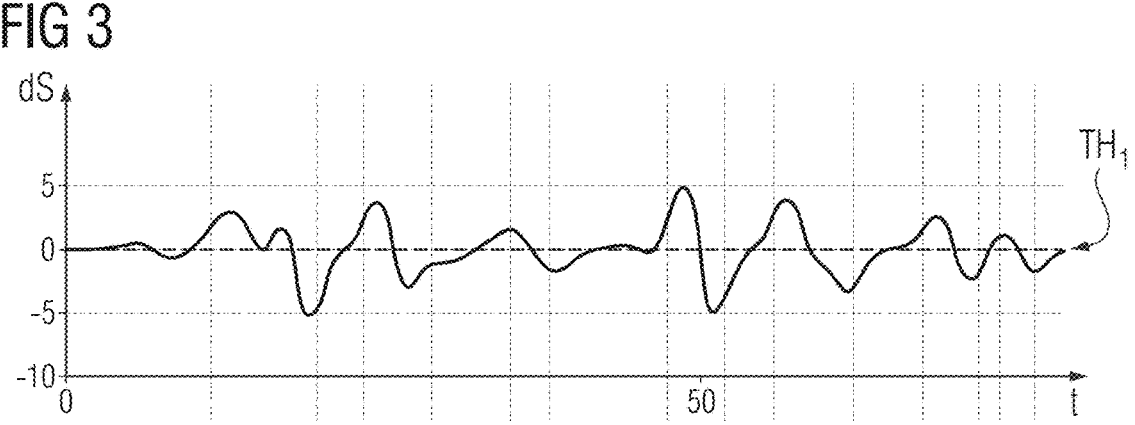
Figure 4:
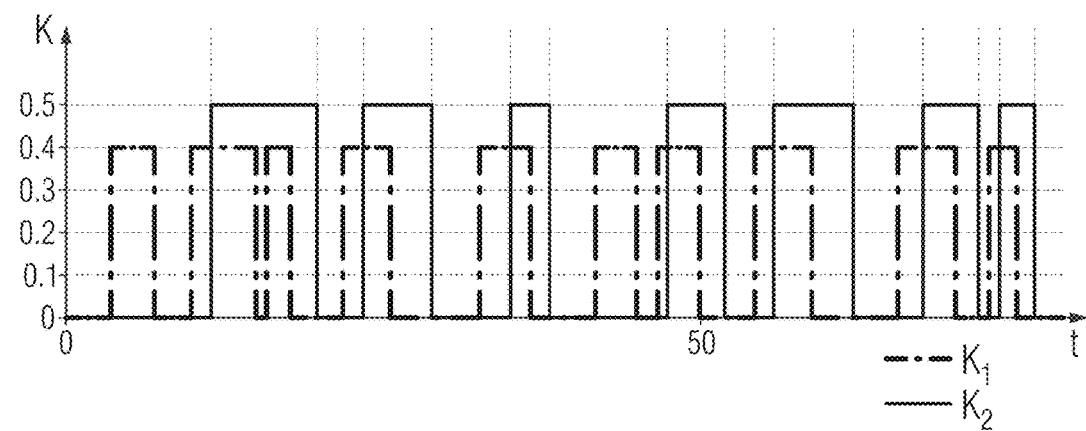

FIGS. 2 to 4 are intended to illustrate the signals that are generated in the photon-counting X-ray detector over time t. FIG. 2 illustrates the signal S that is output during this by a pulse-generating unit 6, as signal pulses in response to incident X-ray photons. Here, the bars that are drawn in illustrate individual photon events, wherein the height of the bars correlates with an energy of the incident photons and hence the energy deposition in the converter element 4. Here, the scale of the signals and bars is selected in particular for the purpose of illustration.

With a high level of photon flux, it is possible for incident photon events that succeed one another rapidly to result in overlaying of the signal pulses S generated by the pulse-generating unit 6—as illustrated in FIG. 2. Conventionally, the number of incident photons are counted in a photon-counting X-ray detector in that the generated electrical signal pulses S are compared with a threshold value TH2 by a comparator 81, and if the threshold value TH2 is exceeded a count signal is output in the form of a binary signal K2 (see illustration of the output signal K of a comparator 81, 8 in FIG. 4). This may be counted via a downstream counter 144, for example constructed as a rising-edge counter or falling-edge counter, and stored temporarily until the count is read off at the time of a respective read-off of the X-ray detector. The vertical dotted lines in FIG. 2 each mark the point in time at which the generated signal pulses S pass through the threshold TH2. These are drawn in in FIGS. 3 and 4. The length of a binary signal K2 in FIG. 4 corresponds in each case to the period for which the signal pulse S lies above the threshold value TH2. If a plurality of comparators 81 with a plurality of threshold values TH2, which can be set differently, are provided for comparing the generated signals S, then information on energy can also be obtained. Measuring the period for which the threshold is exceeded can also allow conclusions on energy information to be drawn.

If a primary signal pulse S does not fall below the threshold value TH2 again before it is succeeded by a signal pulse S, however, it is not possible to distinguish between the signal pulses S of successive photon events in this way. In the event of a high level of flux, this results in false values for the counted number, and can even lead to complete paralysis of the detector.

FIG. 3 shows the differentiated signal dS from FIG. 2, as it may be output by a differentiator unit 10 according to the invention, wherein the differentiated signal dS corresponds to the derivative of the signal S and hence mirrors the course of the rise in the signal S over time t. According to the invention, this is compared with a threshold value TH1, via a comparator 8 coupled to the differentiator unit 10, and a binary signal K1 based on the comparison is output (see also FIG. 4).

The binary comparator output signal K1 based on the differentiated signal is set to high as long as the differentiator signal lies above the threshold value TH1. Via analyzing the differentiated signal dS, it is possible to detect changes in the rise of the signal pulses S generated by the pulse-generating unit P. If for example the signal pulse rises again in the event of overlaying, this can be detected via the differentiated signal dS and the comparator output signal K1 based on it, even if the generated signal pulse S has not fallen below the threshold TH2 again.

It is not possible to detect every instance of overlaying in this way, but using the differentiated signal dS it is possible to provide information that—in contrast to the signal S—is more independent of overlaying effects right up to relatively high levels of photon flux—that is to say has better linearity behavior right up to relatively high levels of photon flux. In the case shown, it would seem that this applies for example at least to the sixth photon event from the left in FIG. 2, which in FIG. 4 is converted to a binary signal K1 based on the differentiated signal, but which cannot be detected as a separate event via the binary signal K2 (which is based only on the output signal S of the pulse-generating unit 6).

Here, the selection of the logic state in FIG. 4 as high (logic state 1) or low (logic state 0) is made arbitrarily, and corresponds substantially to a conventional conversion.

Figure 5:
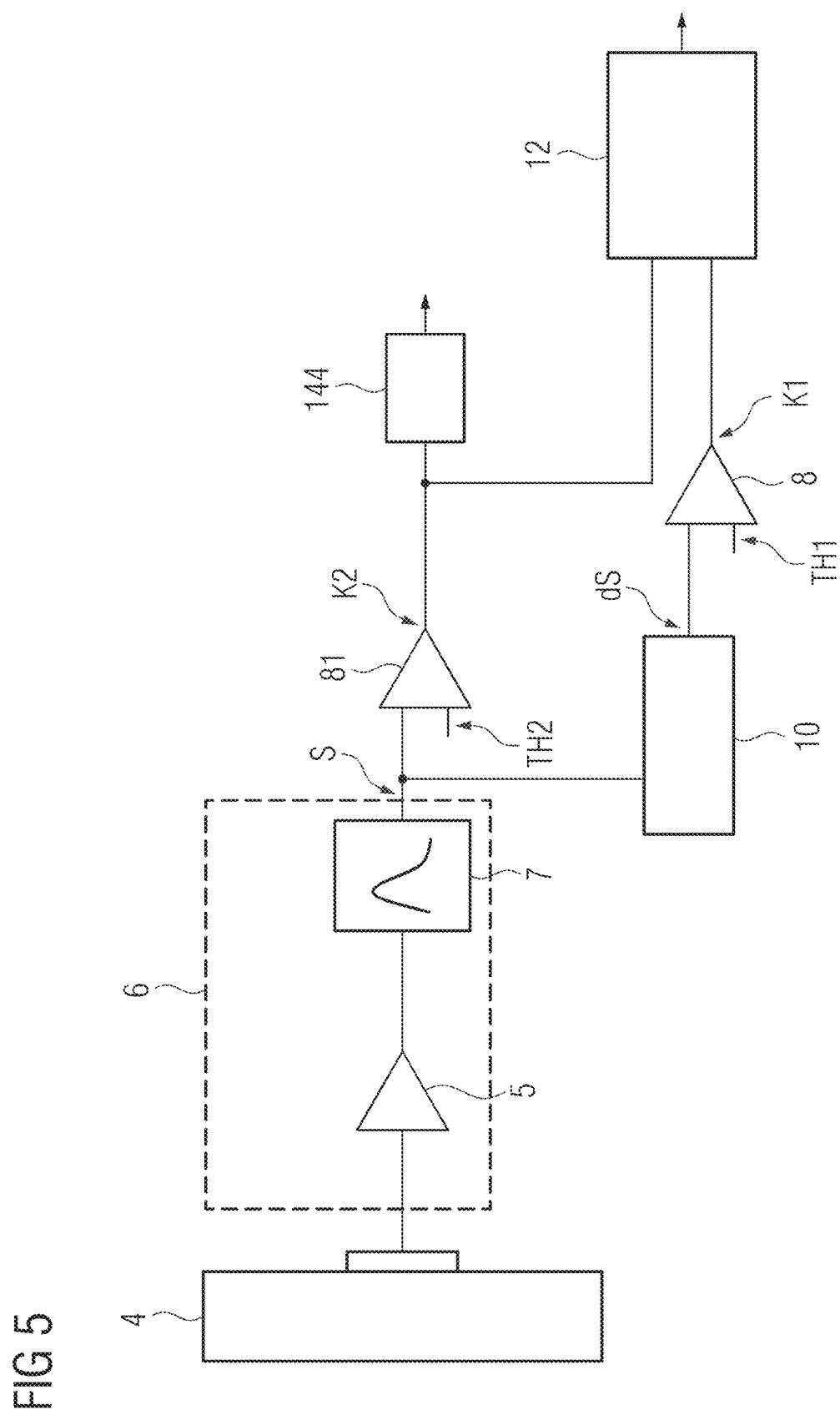
FIG. 5 shows a schematic representation of a signal processing cascade in a first variant, via a photon-counting X-ray detector.

FIG. 5 shows a variant embodiment of a processing cascade provided by a photon-counting X-ray detector according to an embodiment of the invention, with reference to the essential processing units. A processing cascade of this kind may in particular be provided for each pixel element of an X-ray detector or at least for a selection of pixel elements of a plurality of pixel elements of the photon-counting X-ray detector.

The evaluation unit 2 of the photon-counting X-ray detector in this case has the pulse-generating unit 6, which is constructed to output a signal pulse S based upon the electrical signal that is fed from the converter element 4. The pulse-generating unit 6 may have an amplifier 5, for amplifying the fed electrical signal, and a pulse shaper 7 for shaping the pulse of the fed amplified signal, such that at the output of the pulse-generating unit 6 there may be output an analog electrical signal pulse S that correlates with the deposited energy in the converter element 4.

The generated signal pulse S is output to the differentiator unit 10, which provides a differentiated signal dS and that is output to the first comparator 8. The comparator is constructed to compare the differentiated signal dS with a set first threshold value TH1 and to output a first binary signal K1.

Moreover, in this example variant embodiment, the evaluation unit 2 has a second comparator 81 that is coupled to the pulse-generating unit 6 and is constructed to compare the electrical signal pulse S generated by the pulse-generating unit 6 with a second threshold value TH2 and, on this basis, to output a second binary signal K2 for the period for which the threshold is exceeded.

Based on the second binary signal K2, via a counter 144 for example in the manner of a conventional photon-counting X-ray detector, a number of signal pulses S that exceed the second threshold value TH2 may be determined.

Moreover, in the illustrated variant, the photon-counting X-ray detector has a determination unit 12 that is constructed to determine, at least while an electrical pulse S generated by the pulse-generating unit 6 lies above the second threshold value TH2 of the second comparator 8, a sequence of the binary signal K1 of the differentiator unit 10.

The sequence may comprise the course of the high or low state, as illustrated in FIG. 4, over time. The sequence may for example comprise a number of rising and falling edges of the first binary signal K1.

By determining the sequence while a signal exceeds the second threshold TH2, it is possible to restrict it to the signals S that exceed the threshold TH2 and hence are to be detected as a count signal, whereas signals that do not exceed the threshold TH2 are filtered out.

By analyzing the sequence of the first binary signal, it is possible to make an inference of events that are not counted using a regular count based on the signal pulse that is directly output by the pulse-generating unit and the associated second binary signal.

Moreover, outputting and storing the determined sequence in a storage unit may advantageously allow subsequent correction within the context of a post-processing of detected count rates, based on the electrical pulses that are generated via the pulse-generating unit.

Figure 6:
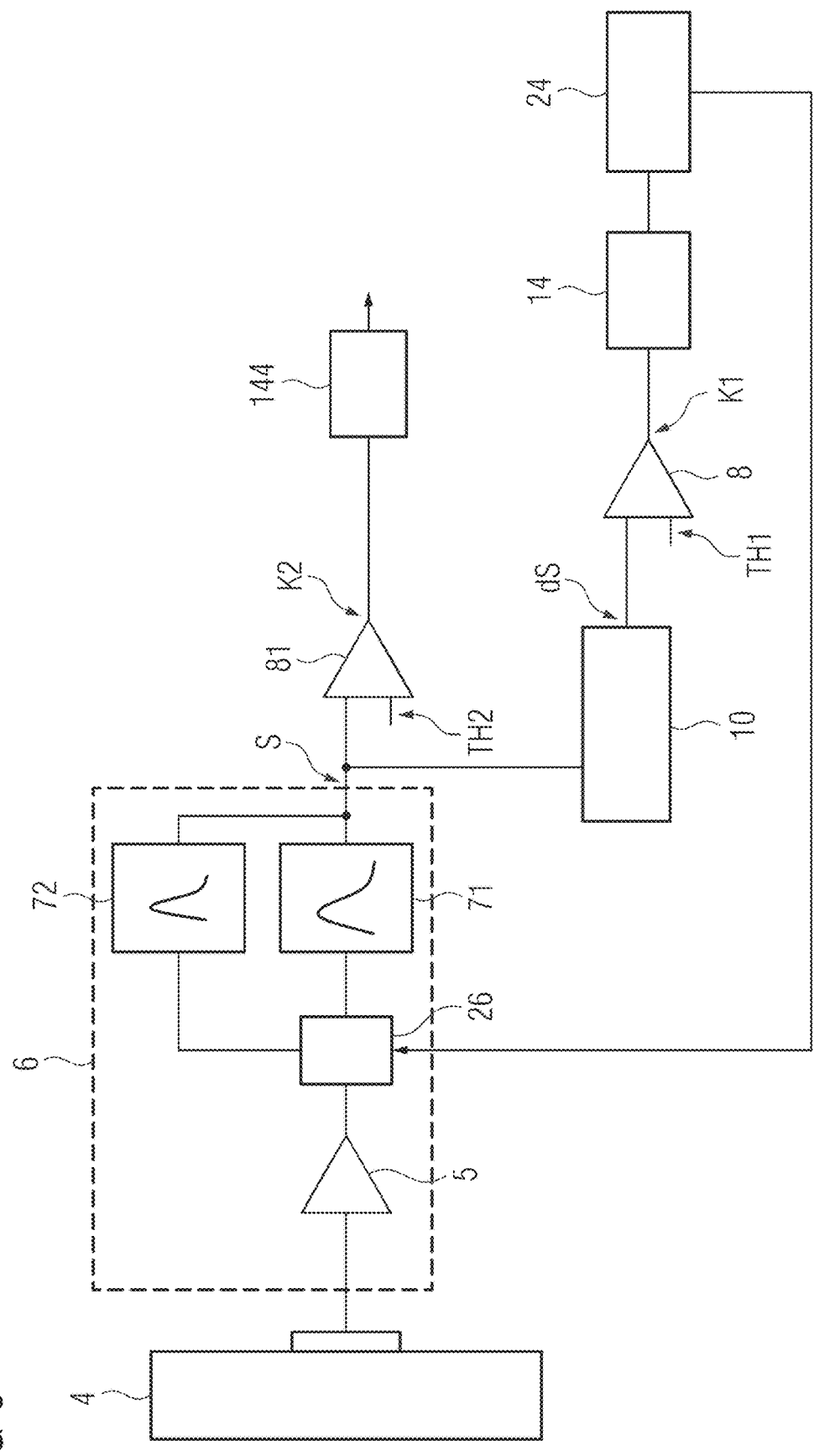
FIG. 6 shows a schematic representation of a signal processing cascade in a second variant, via a photon-counting X-ray detector.

FIG. 6 shows a further variant embodiment of a processing cascade provided by a photon-counting X-ray detector according to the invention, with reference to the essential processing units. The photon-counting X-ray detector according to the invention also has a counter 14, which is coupled to the first comparator 8 and is constructed to count a number of rising or falling edges of binary output signals K1 that are output by the first comparator 8.

Moreover, in the example variant embodiment shown, the photon-counting X-ray detector has an adapter unit 24, which, based upon the number of rising or falling edges counted by the first counter 14, is constructed to adapt generation of the electrical pulses S in the pulse-generating unit 6. In this way, it is possible to adapt the pulse generation in dependence on the incident photon flux. For example, one or more threshold numbers of counted rising or falling edges may be stored, and if this or these is/are exceeded or fallen below an adaptation of the pulse-generating unit 6 via the adapter unit 24 is triggered.

The example shown in FIG. 6 represents a preferred development of a general adapter unit 24. Wherein the pulse-generating unit has a first pulse generation channel 71 in the form of a first pulse shaper 71, and a second pulse generation channel 72 in the form of a second pulse shaper 72, and a switch element 26. For the purpose of generating the electrical pulses S, the switch element is constructed to switch at least between the first pulse generation channel 71 and the second pulse generation channel 72. The adapter unit 24 is constructed, based upon the number of rising or falling edges counted by the first counter 14, to switch the switch element 26 and thus to achieve adaptation of the pulse-generating unit.

The second pulse shaper 72 may have a shorter signal shaping time than the first pulse shaper 71, and hence generate shorter signal pulses S. Shortening the duration of signal pulses can contribute to better behavior of the X-ray detector with high levels of flux, and hence a better number of incident photons counted using a counter 144, although a deterioration in the electronic noise and possibly in energy resolution have also to be accepted.

Figure 7:
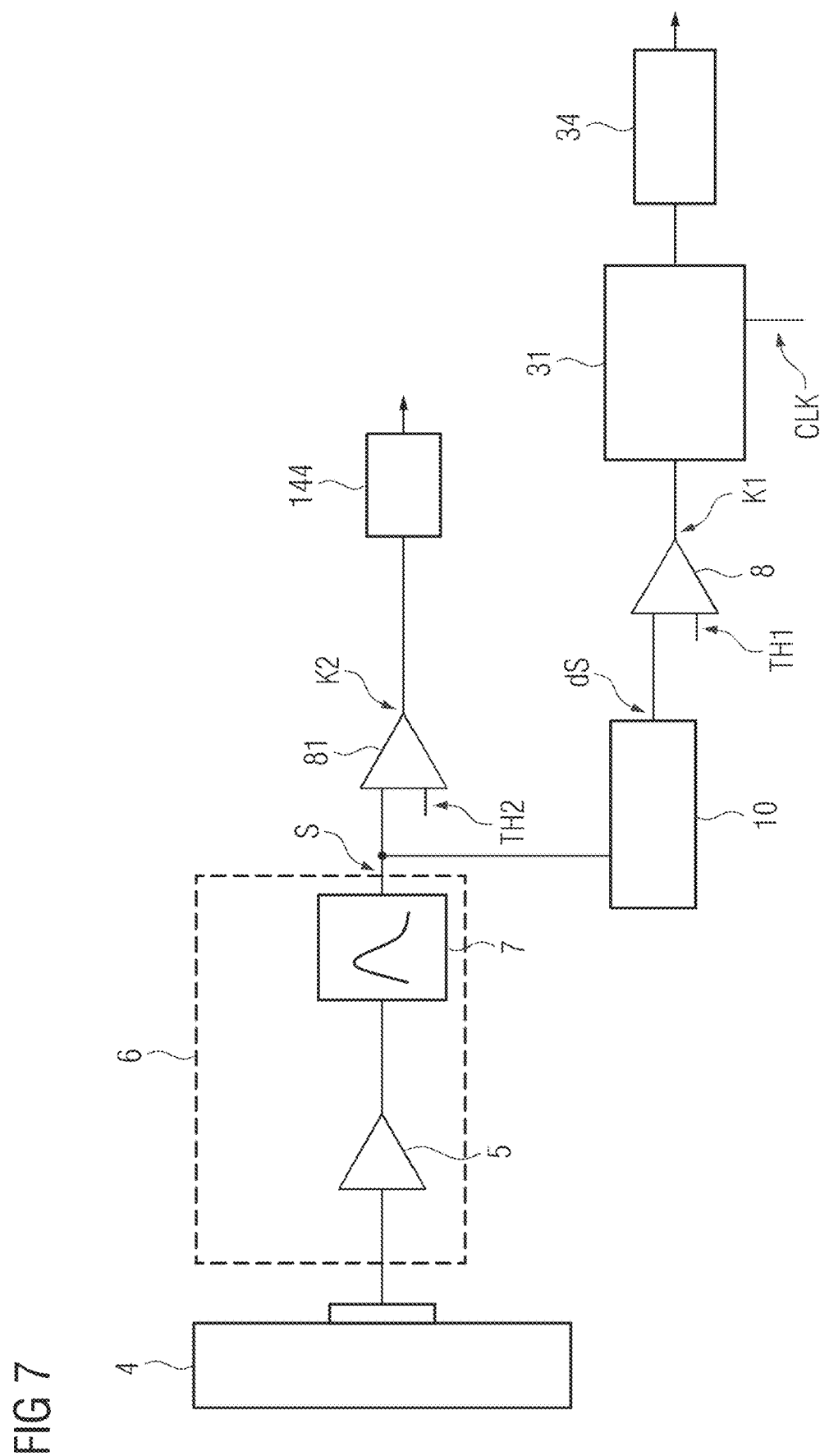
FIG. 7 shows a schematic representation of a signal processing cascade in a third variant, via a photon-counting X-ray detector.

FIG. 7 shows a further schematic representation of a variant embodiment of the photon-counting X-ray detector, wherein the evaluation unit 2 is moreover constructed to determine the respective duration of a binary output signal K1 that is output by the first comparator 8.

In the case shown, the evaluation unit 2 has a pulse-duration determining unit 31. For example, the pulse-duration determining unit 31 may take a form as for a time-over-threshold method, which is widely known in the specialist field of photon-counting X-ray detectors, wherein a pulsed reference signal CLK of fixed frequency is input and the number of pulses of the reference signal CLK that overlap with the binary signal K1 output by the comparator 8 in, by way of example, the high state is counted, as a result of which a duration of the binary signal K1 can be determined.

Furthermore, the X-ray detector is moreover equipped with a defining unit 34, which is constructed to define an integral over the durations or an average of the durations of a plurality of successive binary output signals K1 within a time interval. The time interval may in particular correspond to a read-off time window of the X-ray detector.

Figure 8:
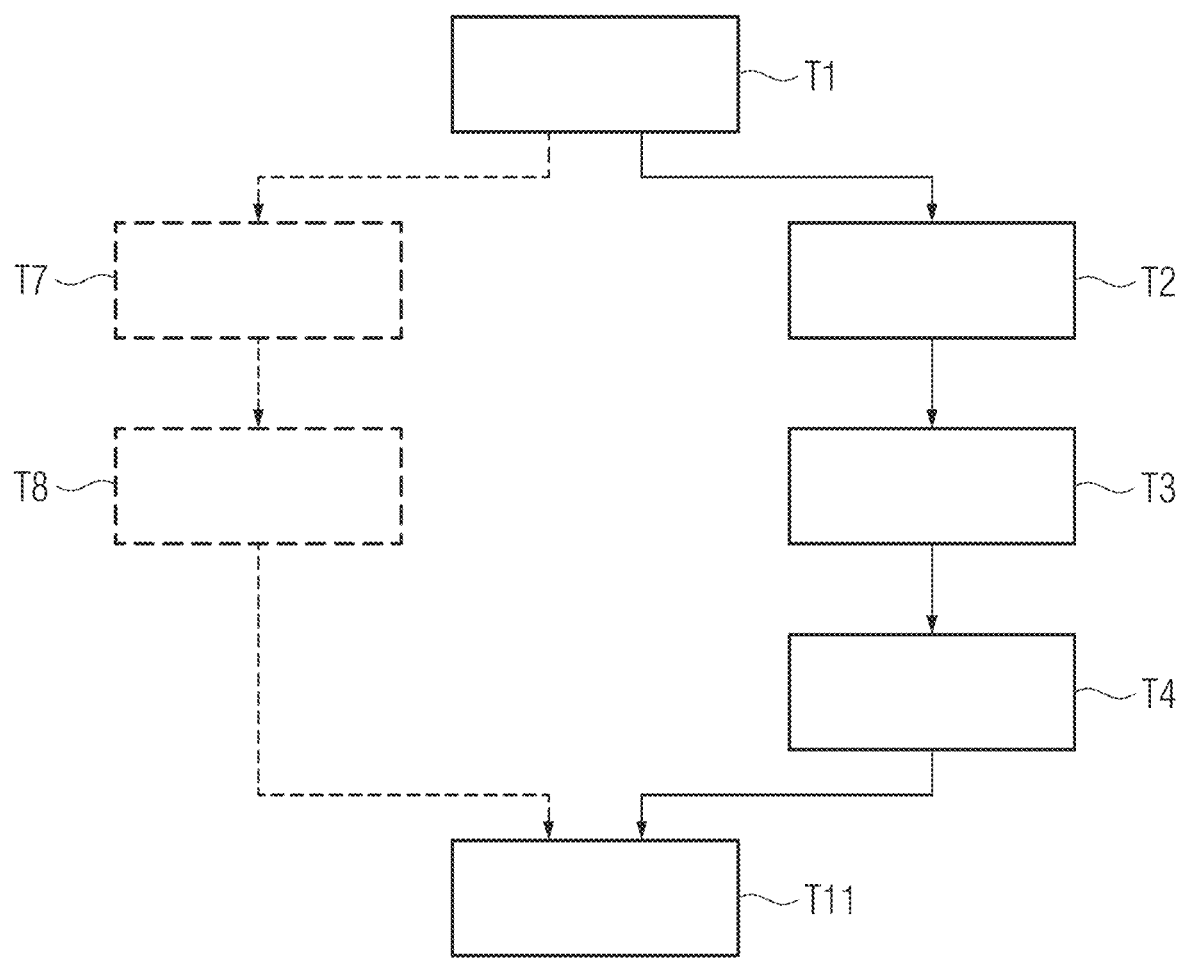
FIG. 8 shows a schematic representation of a method sequence for generating an X-ray image data set via a photon-counting X-ray detector, according to a first variant.

FIG. 8 shows a schematic method sequence in which, in an example variant embodiment of the method, the determined durations can be input for generating an X-ray image data set via the already above-described photon-counting X-ray detector. Here, each pixel element of the X-ray detector may have the processing cascade described in FIG. 7.

In the method sequence shown, in a step T1 electrical pulses S are generated via a pulse-generating unit 6 based upon electrical signals fed from the converter element 4.

In a first processing path, in a step T7 the generated electrical pulses S are compared with a threshold value TH2 via a comparator 81 that is coupled to the pulse-generating unit 6, and based upon this a binary output signal K2 is output, as a count signal that is counted in a step T8 via a counter 144. This may be based in particular on counting a number of rising or falling edges of the binary output signal. The counted number of count signals in the pixel elements of the X-ray detector can then be processed, in a processing step T11, for the purpose of generating the X-ray image data set. It is clear that this first processing path substantially corresponds to conventional processing, known in the specialist field, of signals generated by a photon-counting X-ray detector. In this case, it is likewise possible to provide a plurality of comparators 81 with a plurality of threshold values TH2 that can be set differently, for energy-resolved measurements, with the result that in the processing step T11 it is possible to draw on energy-resolved measurement data in order to generate the X-ray image data set.

In a second processing path, in a step T2 a differentiated signal dS of the pulses S generated by the pulse-generating unit 6 is generated via a differentiator unit 10 coupled thereto. In a step T3, the differentiated signal dS is compared with a threshold value TH1 via a comparator 8 that is coupled to the differentiator unit 10, and based upon the comparison a binary output signal K1 is output for a period for which the threshold value is exceeded.

Furthermore in the present example, in a step T4 an integral or an average value of the durations of a plurality of successive binary output signals K1 from the first comparator 8 is defined via the defining unit 34, and the X-ray image data set is then generated in the processing step T11 based upon the integral or average value.

For example, the first processing path is part of standard processing. However, at very high levels of flux, in which the standard processing path no longer delivers reliable image data because of pronounced pile-up effects, it is possible to draw on the second processing path or the measurement data resulting therefrom, wherein image data can be generated based upon an integral or average value of the durations in the pixel elements, based on the differentiated signal. The inventors have seen that this value may have a high degree of correlation with the energy flux of the X-ray field, and in particular in the event of a high level of flux can provide information that is similar to a conventional energy-integrating detector. This can be used particularly advantageously if conventional processing based directly on the signals S generated by the pulse-generating unit 6 no longer, or only to a small extent, ensures reliable image information. In this case, measurement data can be collected on both paths during a measurement sequence, and a decision on use of the measurement data can be made only subsequently, after a measurement sequence. Similarly, it is also possible to provide for switchover between the processing paths even while a measurement sequence is still going on, for example with reference to a threshold value stored in the X-ray detector and relating to a counted number of counted pulses per unit time.

Likewise, combined processing to form an X-ray image data set is conceivable, wherein both a conventional count signal, based on the pulses S generated by the pulse-generating unit 6, and also one based on processing of the differentiated signal dS, is drawn on. For example as a boundary condition in an iterative image reconstruction procedure, or as an input parameter of a machine learning system that is trained for image reconstruction, for example a neural network.

Figure 9:
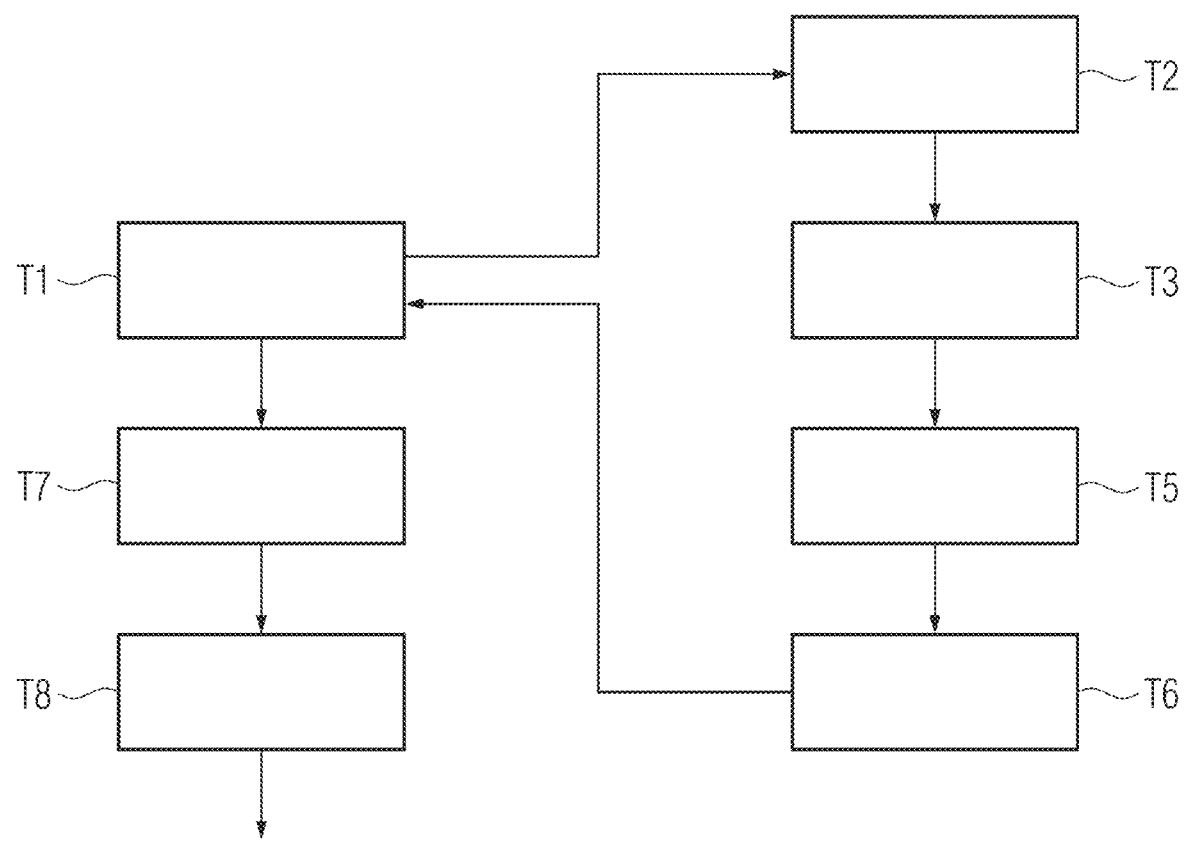
FIG. 9 shows a schematic representation of a method sequence for generating an X-ray image data set via a photon-counting X-ray detector, according to a second variant.

FIG. 9 shows a further example variant embodiment of a method for generating an X-ray image data set, which comprises adaptation of the pulse-generating unit 6 of the photon-counting X-ray detector. The X-ray detector used for this may have for example an adapter unit 24 that can switch between switchable pulse generation channels 71, 72, in each pixel element of the X-ray detector, as described with reference to FIG. 6.

After a step T3, in which the differentiated signal dS is compared with a threshold value TH1 via a comparator 8 that is coupled to the differentiator unit 10, and based upon the comparison a binary output signal K1 is output for a period for which the threshold value TH1 is exceeded, the method moreover comprises the step T5, in which a number of rising or falling edges of binary output signals K1 that are output by the first comparator K1 are counted via a counter 14 coupled to the first comparator 8, and the step T6, in which generation of the electrical pulses in the pulse-generating unit 6 is adapted via the adapter unit 24 based upon the number of rising or falling edges that are counted.

The adapted signal pulses S that are generated via the pulse-generating unit 6 can then in turn be compared with a second threshold value in a step T7 and counted in a step T8 in order, as the procedure continues, to be processed in a processing step T11 in order to generate the X-ray image data set. That is to say, an X-ray image data set can be generated based upon the adapted signal pulses S. In this way, an adaptation of the X-ray detector can be adapted to currently prevailing conditions in respect of a photon flux.

Figure 10:
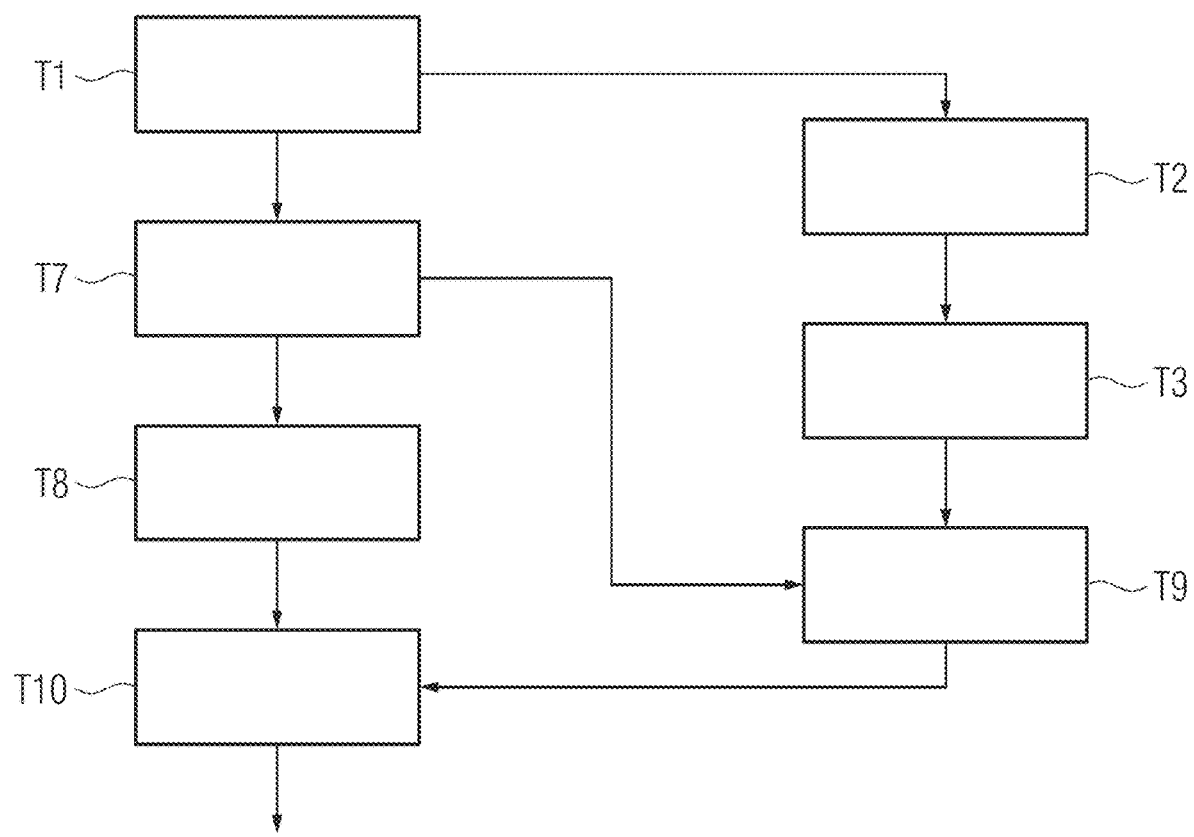
FIG. 10 shows a schematic representation of a method sequence for generating an X-ray image data set via a photon-counting X-ray detector, according to a third variant.

FIG. 10 shows a further example variant embodiment of a method for generating an X-ray image data set, wherein a sequence of the first binary output signal K1 is determined. The photon-counting X-ray detector that is used for this may have for example a determination unit 12 for each pixel element, as described in relation to FIG. 5.

In this variant, in a step T9, via the determination unit 12 a sequence of the first binary output signal K1 is determined at least while an electrical pulse S that is generated by the pulse-generating unit 6 lies above the second threshold value TH2 of the second comparator 81, and in a step T10 the number of generated electrical pulses S that have been counted in step T8 by a counter 144 is adapted, in particular corrected. This may be done for example by a comparison between the number that are counted based upon the second binary signal K2, and the number of high states of the first binary signal K1, with reference to the determined sequence. Based upon the adapted number, it is then possible to generate an X-ray image data set. The adapted number may for example be processed, as the method continues, in a step T11 for generating the X-ray image data set.

The described variants may in particular also be combined with a plurality of second comparators and second threshold values TH2.

In the last variant, for example a sequence of the first binary signal may in this case be determined individually in dependence on each second threshold TH2, and a direct adaptation of the numbers that are counted in dependence on the second thresholds TH2 may be performed. As an alternative, it is also possible to determine only one sequence in dependence on a lowest-energy threshold TH2, and on this basis to define an estimated correction factor for the counted numbers of the further, higher-energy thresholds TH2. The estimate may be based for example on previous experiments and, defined from these, functional dependencies.

Figure 11:
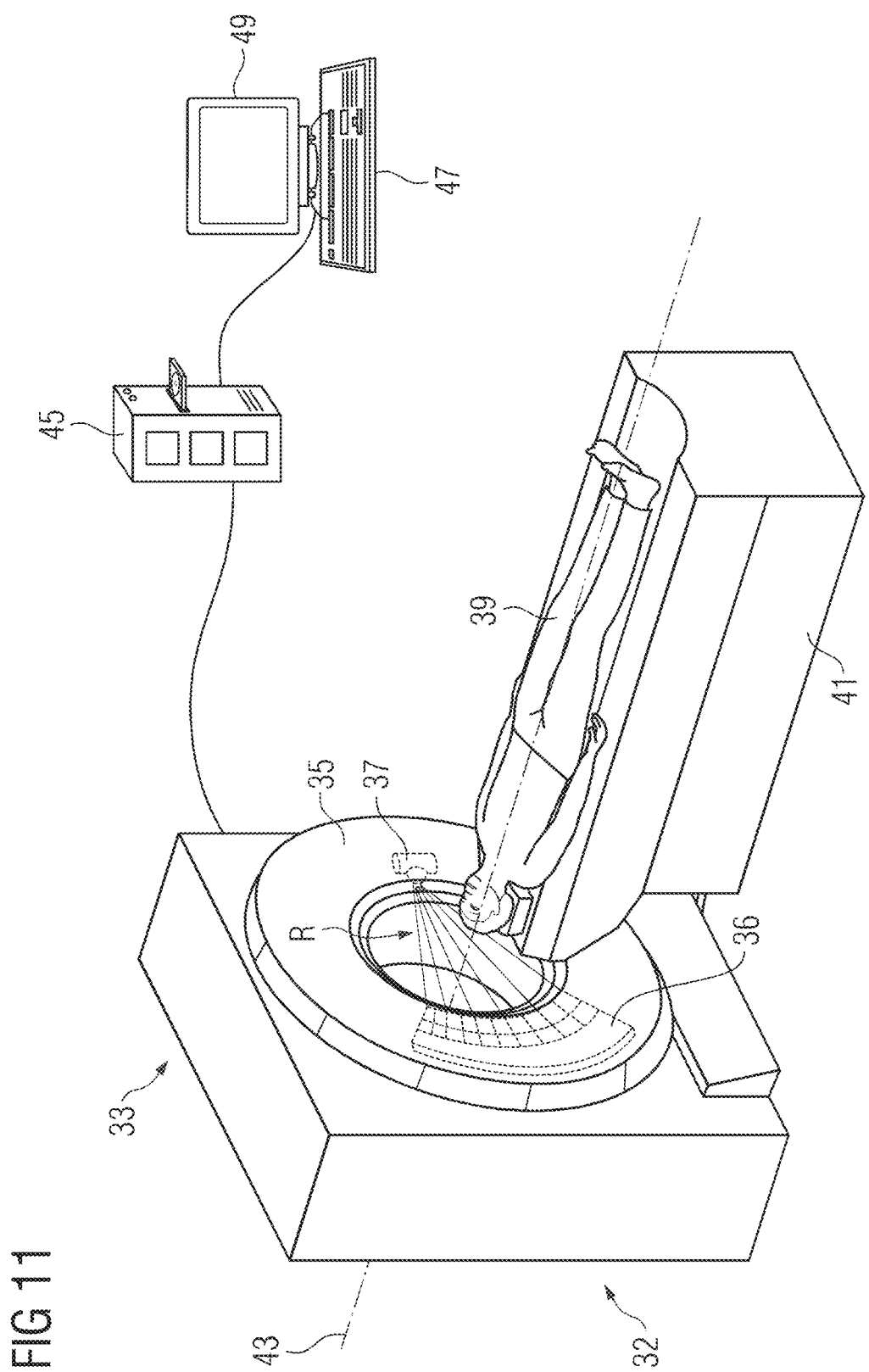
FIG. 11 shows a schematic representation of a medical imaging device in the form of a computed tomography device.

FIG. 11 shows an example embodiment of a medical imaging device 32, having a detection unit 36 comprising at least one photon-counting X-ray detector according to the invention and an X-ray source 37 opposite the detection unit 36. The X-ray source is constructed to expose the detection unit 36 and hence the X-ray detector to X-rays along a direction of incidence of X-rays. The medical imaging device 32 that is shown in particular takes the form of a computed tomography system. The computed tomography system contains a gantry 33 with a rotor 35. The rotor 35 comprises the X-ray source 37 and the detection unit 36. The rotor 35 is rotatable about the axis of rotation 43. The object undergoing examination 39, in this case a patient, is borne on a patient table 41 and movable through the gantry 33 along the axis of rotation 43. For the purpose of controlling the computed tomography system and for the purpose of further processing the measurement data read off from the detection unit 36, in order to generate an X-ray image data set that maps the object 39, it is possible to use a processor unit 45. An input facility 47 and an output apparatus 49 are connected to the processor unit 45, which makes it possible for a user to interact with the medical imaging device and for a generated X-ray image data set to be displayed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A photon-counting X-ray detector, comprising:
   an X-ray detector configured to convert incident X-rays into electrical signals; and
   an evaluation device coupled to the X-ray detector, the evaluation device including
      a pulse-generator configured to generate and output an electrical pulse based on an electrical signal from the X-ray detector,
      a differentiator coupled to the pulse-generator, the differentiator being configured to generate a differentiated signal of the electrical pulse, and
      a first comparator coupled to the differentiator, the first comparator being configured to compare the differentiated signal with a first threshold value, and output a binary output signal based on the comparison, the binary output signal being output for a first period of time corresponding to a second period of time during which the first threshold value is exceeded by the differentiated signal, wherein
      the evaluation device is configured to determine a duration of the binary output signal, and
      the photon-counting X-ray detector is configured to define an integral over a plurality of durations of a plurality of binary output signals output from the first comparator or define an average of the plurality of durations, the plurality of binary output signals being successive and within a time interval.

2. The photon-counting X-ray detector of claim 1, wherein
   the evaluation device further includes a second comparator coupled to the pulse-generator, the second comparator being configured to compare the electrical pulse with a second threshold value, and
   the photon-counting X-ray detector is configured to determine a sequence of the plurality of binary output signals while the electrical pulse is above the second threshold value.

3. The photon-counting X-ray detector of claim 2, further comprising:
   a first counter coupled to the first comparator, the first counter being configured to count a number of rising or falling edges of the plurality of binary output signals.

4. The photon-counting X-ray detector of claim 3, further comprising:
   an adapter configured to adapt generation of electrical pulses based on the number of rising or falling edges.

5. The photon-counting X-ray detector of claim 4, wherein
   the pulse-generator includes a first pulse generation channel, a second pulse generation channel, and a switch, and
   the adapter is configured to control the switch to switch between the first pulse generation channel and the second pulse generation channel based on the number of rising or falling edges.

6. A medical imaging device, comprising:
   the photon-counting X-ray detector of claim 2; and
   an X-ray source configured to expose the photon-counting X-ray detector to X-rays.

7. The photon-counting X-ray detector of claim 1, further comprising:
   a first counter coupled to the first comparator, the first counter being configured to count a number of rising or falling edges of the plurality of binary output signals.

8. The photon-counting X-ray detector of claim 7, further comprising:
   an adapter configured to adapt generation of electrical pulses based on the number of rising or falling edges.

9. The photon-counting X-ray detector of claim 8, wherein
   the pulse-generator includes a first pulse generation channel, a second pulse generation channel, and a switch, and
   the adapter is configured to control the switch to switch between the first pulse generation channel and the second pulse generation channel based on the number of rising or falling edges.

10. A medical imaging device, comprising:
the photon-counting X-ray detector of claim 1; and
an X-ray source configured to expose the photon-counting X-ray detector to X-rays.

11. The medical imaging device of claim 10, wherein the medical image device is a computed tomography device.

12. A method, using a photon-counting X-ray detector including an X-ray detector to convert incident X-rays into electrical signals, and an evaluation unit to process the electrical signals, the method comprising:
  generating, via a pulse-generator, an electrical pulse based on an electrical signal from the X-ray detector;
  generating, via a differentiator, a differentiated signal of the electrical pulse;
  comparing, via a first comparator, the differentiated signal with a first threshold value;
  outputting, via the first comparator, a first binary output signal based on the comparing, the first binary output signal being output for a first period of time corresponding to a second period of time during which the differentiated signal exceeded the first threshold value, wherein the first binary output signal is usable for generation of an X-ray image data set;
  determining a duration of the first binary output signal; and
  defining an integral over a plurality of durations of a plurality of first binary output signals output from the first comparator or defining an average of the plurality of durations, the plurality of first binary output signals being successive and within a time interval.

13. The method of claim 12, further comprising:
  counting, via a counter coupled to the first comparator, a number of rising or falling edges of the plurality of first binary output signals; and
  adapting, via an adapter, the generating of electrical pulses based on the number of rising or falling edges.

14. The method of claim 12, further comprising:
  comparing, via a second comparator coupled to the pulse-generator, the electrical pulse with a second threshold value;
  outputting a second binary output signal based on the comparing;
  counting, via a second counter coupled to the second comparator, a number of rising or falling edges of a plurality of second binary output signals;
  determining a sequence of the plurality of first binary output signals while the electrical pulse is above the second threshold value; and
  adapting the number of rising or falling edges to generate the X-ray image data set based on the sequence.

15. A photon-counting X-ray detector, comprising:
an X-ray detector configured to convert a plurality of X-rays into a plurality of electric signals;
processing circuitry configured to cause the photon-counting X-ray detector to
  generate a plurality of electrical pulses based on the plurality of electrical signals,
  generate a plurality of differentiated signals based on the plurality of electrical pulses,
  output a plurality of successive binary output signals based on a comparison between each respective differentiated signal and a threshold value, each of the plurality of successive binary output signals having a duration corresponding to an amount of time the respective differentiated signal exceeds the threshold value,
  define at least one of (i) an integral over durations of the plurality of successive binary output signals within a time interval or (ii) an average of the durations of the plurality of successive binary output signals within the time interval, and
  generate an X-ray image data set based on at least one of the integral over the durations or the average of the durations.

* * * * *